(12) United States Patent
Hashimoto

(10) Patent No.: US 7,308,828 B2
(45) Date of Patent: Dec. 18, 2007

(54) ULTRASONIC PROBE

(75) Inventor: Shinichi Hashimoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 3 days.

(21) Appl. No.: 11/415,156

(22) Filed: May 2, 2006

(65) Prior Publication Data

US 2006/0191344 A1 Aug. 31, 2006

Related U.S. Application Data

(63) Continuation of application No. PCT/JP05/17051, filed on Sep. 15, 2005.

(30) Foreign Application Priority Data

Sep. 24, 2004 (JP) ............... 2004-276612

(51) Int. Cl.
- *A61B 8/00* (2006.01)
- *A61B 8/06* (2006.01)
- *G01N 29/32* (2006.01)
- *G01N 29/24* (2006.01)

(52) U.S. Cl. ............ 73/617; 73/632; 600/437; 600/459

(58) Field of Classification Search ............ 73/617, 73/632

See application file for complete search history.

(56) References Cited

U.S. PATENT DOCUMENTS

| 5,046,365 | A | * | 9/1991 | Kumley et al. | .............. 73/708 |
| 5,560,362 | A | * | 10/1996 | Sliwa et al. | ............... 600/439 |
| 6,624,539 | B1 | * | 9/2003 | Hansen et al. | ............... 310/26 |
| 2004/0002655 | A1 | * | 1/2004 | Bolorforosh et al. | ....... 600/459 |
| 2005/0215892 | A1 | * | 9/2005 | Emery et al. | ............... 600/437 |

FOREIGN PATENT DOCUMENTS

| JP | 59-28951 | 2/1984 |
| JP | 9-140706 | 6/1997 |
| JP | 10-85219 | 4/1998 |
| JP | 10-94540 | 4/1998 |
| JP | 3061292 | 6/1999 |
| JP | 11-299775 | 11/1999 |
| WO | WO 9412873 A1 * | 6/1994 |

\* cited by examiner

*Primary Examiner*—Hezron Williams
*Assistant Examiner*—Rose M Miller
(74) *Attorney, Agent, or Firm*—Oblon, Spivak, McClelland, Maier & Neustadt, P.C.

(57) ABSTRACT

An ultrasonic probe has a probe proper, a connector and a cable for electrically connecting between the probe proper and the connector. The probe proper includes a transducer that converts between ultrasonic wave and electricity, and a phase change member having a property to cause a phase change of from solid to liquid at a particular temperature reached in an operation time period of the transducer and a phase change of from liquid to solid at lower than the particular temperature.

7 Claims, 13 Drawing Sheets

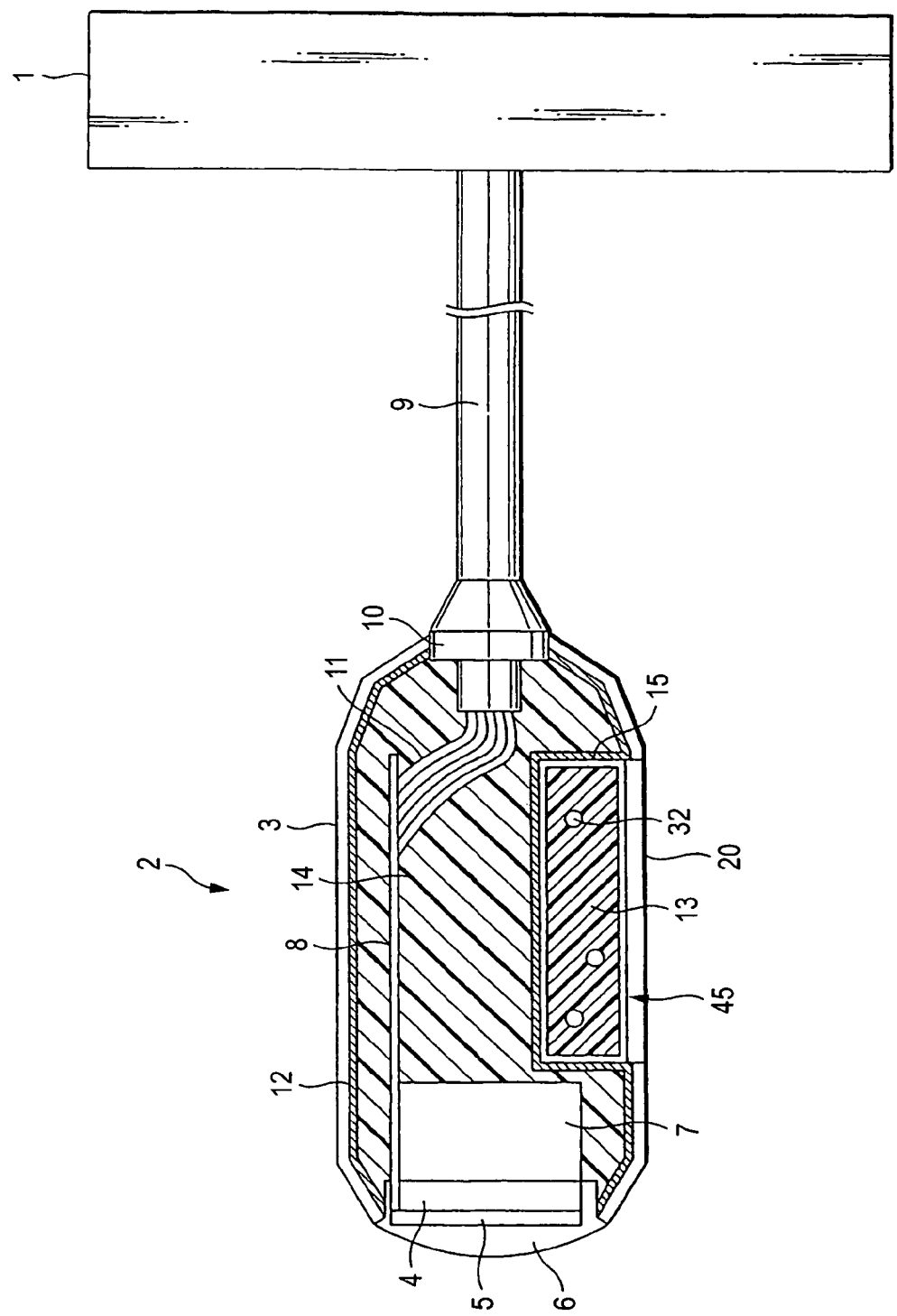

ULTRASONIC PROBE

CROSS-REFERENCE TO RELATED APPLICATIONS

This is a Continuation Application of PCT Application No. PCT/JP2005/017051, filed Sep. 15, 2005, which was published under PCT Article 21(2) in Japanese.

This application is based upon and claims the benefit of priority from prior Japanese Patent Application No. 2004-276612, filed Sep. 24, 2004, the entire contents of which are incorporated herein by reference.

BACKGROUND OF THE INVENTION

1. Field of the Invention

The present invention relates to an ultrasonic probe to be furnished on an ultrasonic diagnostic apparatus.

2. Description of the Related Art

The ultrasonic diagnostic apparatuses are broadly used in the medical field, which are to examine a subject by sending an ultrasonic wave into the subject and receiving a reflection wave, an echo signal, from the subject. The ultrasonic diagnostic apparatus is furnished with an ultrasonic probe for transmitting and receiving an ultrasonic wave. The ultrasonic probe is to be used by an abutment against the examination subject.

The ultrasonic probe structure in the conventional art is explained. As shown in FIG. 11, a probe proper 102 has a probe housing 103. The probe housing 103 accommodates therein a transducer unit 128, a flexible printed-wiring board 108, and a magnetic-shield member 112. The transducer unit 128 is made up with a transducer 104, an acoustic matching layer 105, an acoustic lens 106 and a backing material 107. The transducer 104 has a plurality of transducer elements arranged in one-dimensional or two-dimensional form. The transducer element is made up by a piezoelectric element that is typically a vibrator, a common electrode formed on one surface of the piezoelectric element and a discrete electrode formed on the opposite surface. A plurality of discrete electrodes provided to the plurality of transducer elements are extended by a plurality of signal lines printed on the flexible printed-wiring board 108. The plurality of signal lines are connected to a plurality of cable wires 111. The plurality of cable wires 111 in a bundle constitute a cable 109, cooperatively with a coating of plastic, etc. The cable 109 is extended out of the probe housing 103 through a clamp 110. The probe proper 102 is connected to an external ultrasonic diagnostic apparatus by the connector 101 provided at an end of the cable 109.

The transducer 104 generates heat during the conversion of ultrasonic wave/electricity. The ultrasonic wave generated by the transducer 104 is partly absorbed in the transducer 104. This causes heat. Meanwhile, the flexible printed-wiring board 108 is mounted with an electronic circuit, such as a multiplexer. Heat is generated on the electronic circuit.

The ultrasonic probe is to be put on the surface of a subject. For this reason, the acoustic lens 106, for contact with a subject, has a surface temperature whose upper limit value is set up. Meanwhile, the image S/N obtained in the ultrasonic diagnostic apparatus improves in proportion to the increase of ultrasonic-wave transmission power. Consequently, there is a need to raise the ultrasonic-wave transmission power in a range the surface temperature of the acoustic lens 106 does not reach its upper limit value.

In the conventional countermeasure against heat, there are included a provision of means of transferring the heat, generated at a transducer, to a point distance from the transducer (JP-A-9-140706), a provision of means of conducting the heat, generated at a transducer, to a cable (JP-A-10-94540), and a provision of two kinds of sealing resins (JP-A-10-85219).

However, the drive scheme/condition to send and receive an ultrasonic wave by the ultrasonic diagnostic apparatus is not limited to one but diagnosis is conducted by changing the drive scheme/condition in accordance with diagnostic content from time to time. Accordingly, the heat generated in an ultrasonic probe actually is different in amount depending upon driving scheme/condition.

Meanwhile, there is a need to set a use condition of the ultrasonic probe by assuming a drive scheme/condition and use way to raise temperature the greatest so that temperature can be maintained for safety even under such conditions. Consequently, in a certain case, temperature rise is less under a certain drive scheme/condition wherein there is provided a margin to a safety criterion. Meanwhile, in another drive scheme/condition, temperature rise be significant so that the ultrasonic diagnostic apparatus is used in a situation on a side closer to a safety criterion. In this manner, there is a great difference in safety depending upon drive scheme/condition.

In a certain drive scheme, ultrasonic-probe transmission acoustic power and circuit-board consumption power are suppressed in order to maintain the temperature for safety, thus sacrificing the image quality obtained.

It can be considered to provide a structure the temperature is not ready to change by providing a great specific heat in average to the ultrasonic probe, as an approach to suppress against the temperature rise while taking account of the difference in ultrasonic-probe temperature rise due to the difference in drive scheme/condition. Meanwhile, those light in specific gravity are preferred in order to enhance the operationality of the ultrasonic probe. However, the use of a material having a great specific heat generally requires a greater specific gravity, thus leading to the weight increase in the ultrasonic probe entirety. This increases the burden on the operator who manipulates the ultrasonic probe. It is the general tendency that specific weight increases with increase in specific heat. This makes it impossible to expect a material meeting the both properties.

BRIEF SUMMARY OF THE INVENTION

It is an object of the present invention to effectively suppress the temperature rise exceeding a particular temperature in an ultrasonic probe.

In a first aspect of the invention, there is provided an ultrasonic probe having a probe proper, a connector and a cable for electrically connecting between the probe proper and the connector, the ultrasonic probe wherein the probe proper comprises: a transducer that converts between ultrasonic wave and electricity; and a phase change member having a property to cause a phase change of from solid to liquid at a particular temperature reached in an operation time period of the transducer and a phase change of from liquid to solid at lower than the particular temperature.

In a second aspect of the invention, there is provided an ultrasonic probe having a probe proper, a connector and a cable for electrically connecting between the probe proper and the connector, the ultrasonic probe wherein the probe proper comprises: a transducer that converts between ultrasonic wave and electricity; a thermal buffering agent that buffers the transducer from rising in temperature exceeding a particular temperature; a probe housing accommodating the transducer and the thermal buffering agent; and a filler agent charged in the probe housing.

In a third aspect of the invention, there is provided an ultrasonic probe having a probe proper, a connector and a cable for electrically connecting between the probe proper and the connector, the ultrasonic probe wherein the probe proper comprises: a transducer that converts between ultrasonic wave and electricity; a thermal delaying agent that delays a transition of the transducer from a state reached a particular temperature to a state the particular temperature is exceeded; a probe housing accommodating the transducer and the thermal delaying agent; and a filler agent charged in the probe housing.

BRIEF DESCRIPTION OF THE SEVERAL VIEWS OF THE DRAWING

FIG. 8A is a sectional view showing an interior schematic structure of an ultrasonic probe according to a sixth embodiment in the invention.

DETAILED DESCRIPTION OF THE INVENTION

Embodiments of the present invention will now be explained in the following.

First Embodiment

Figure 1:
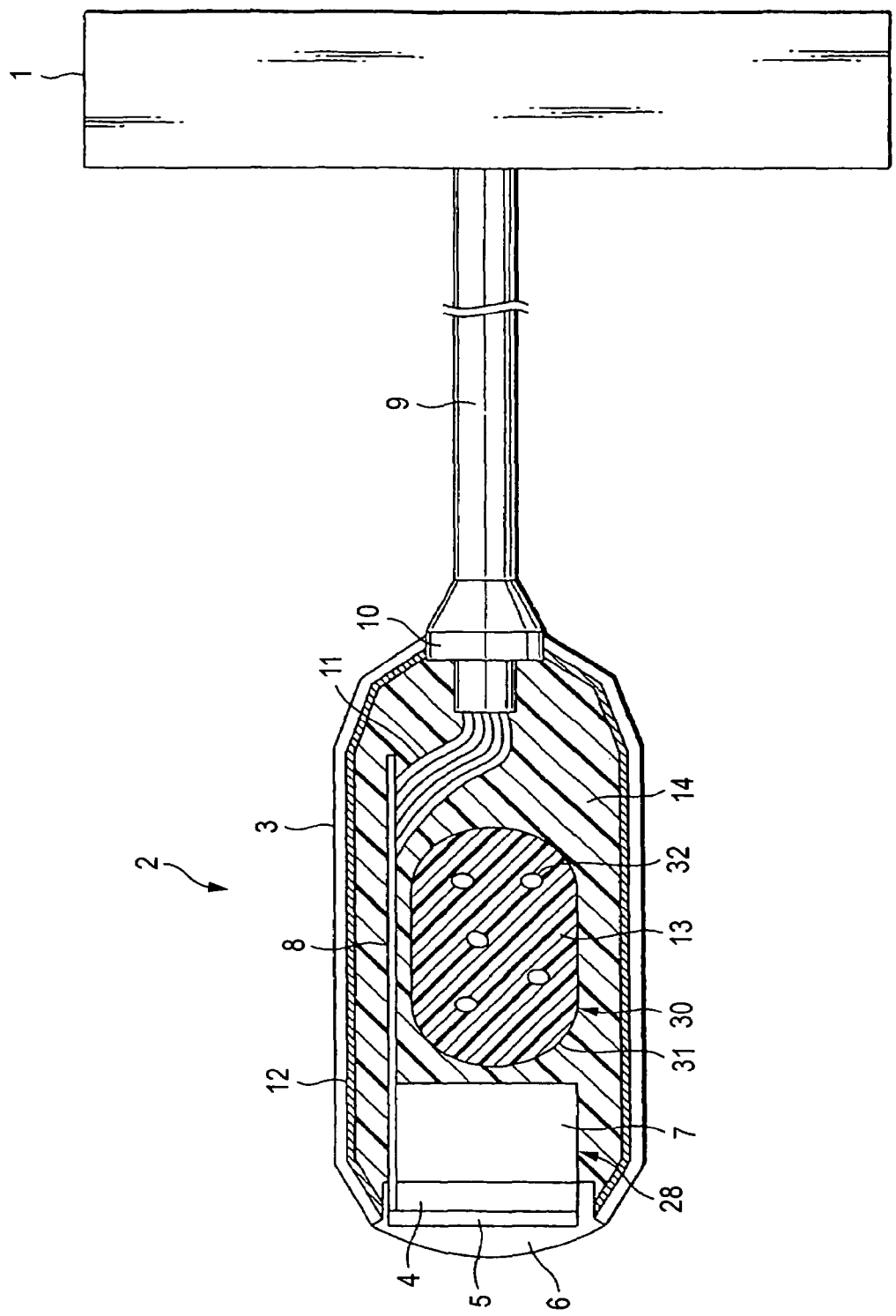
FIG. 1 is a sectional view showing an interior schematic structure of an ultrasonic probe according to a first embodiment in the present invention.

As shown in FIG. 1, a probe proper 2 has a probe housing 3. The probe housing 3 accommodates therein a transducer circuit 28, a flexible printed-wiring board 8 and a magnetic-shield member 12. The probe housing 3 has an interior surface over which is spread a magnetic-shield member 12 made by a metal film, metal mesh or metal case in order to shield the interior from a disturbance radio wave. A transducer unit 28 is made up with a transducer 4, an acoustic matching layer 5, an acoustic lens 6 and a backing material 107. The backing material 107 is arranged in back of the transducer 4. The acoustic matching layer 5 is arranged in front of the transducer 4. The acoustic matching layer 5 is provided to reduce the propagation loss of an ultrasonic wave. The acoustic lens 6 is arranged in front of the acoustic matching layer 5. The acoustic lens 6 is provided to converge an ultrasonic wave. The acoustic lens 6 is fit in an aperture formed in a tip of the probe housing 3. During examination, the acoustic lens 6 at its surface is placed in contact with the surface of an examination subject.

The transducer 4 is made up by a plurality of transducer elements arranged in a one-dimensional or two-dimensional form. The transducer element is typically formed with a piezoelectric element of piezoelectric ceramics, a common electrode formed by baking, evaporation or plating on one surface of the piezoelectric element, and a discrete electrode formed on the opposite surface thereof. The discrete electrode in plurality, possessed by the plurality of transducer elements, are extended by a plurality of signal lines printed on the flexible printed-wiring board 8. The plurality of signal lines are connected to a plurality of cable wires 11. The plurality of cable wires bundled cooperate with a coating of plastic, etc., to constitute a cable 9. The cable 9 is extended out of the probe housing 3 through a clamp 10. The probe proper 2 is connected to an external ultrasonic diagnostic apparatus by means of a connector 1 provided at an end of the cable 9.

Incidentally, an electronic circuit, typically a multiplexer, may be mounted on the flexible printer-wiring board 8. The multiplexer is provided in order to switch over the connection of between the plurality of signal lines for connection to the plurality of transducer elements and the plurality of cable wires 11.

A radio-frequency voltage signal is applied from a pulser of the external ultrasonic diagnostic apparatus to between the electrodes of the transducer elements of the transducer 4, through the connector 1, cable 9 and signal lines. The piezoelectric elements, of the transducer elements of the transducer 4, are caused to mechanically vibrate on the radio-frequency voltage signal. This generates an ultrasonic wave. Meanwhile, the reflection wave from the examination subject causes the piezoelectric element to vibrate mechanically. This generates a voltage at between the electrodes of the transducer elements. The voltage signal generated is supplied to the external ultrasonic diagnostic apparatus through the signal lines, cable 9 and connector 1.

The ultrasonic diagnostic apparatus has at least one of B-mode, Doppler-mode and color-mode processing systems. The B-mode processing system is configured to perform the processing of envelope detection, logarithmic compression, intensity modulation and the like. The Doppler-mode processing system is configured to perform orthogonal detection, Doppler-shift-frequency component extraction, filtering, FFT processing and so on. The color-mode processing system is configured to perform orthogonal detection, filtering, autocorrelation operation, flow-speed/dispersion operation, etc. The image, produced by the B-mode processing system, Doppler-mode processing system or color-mode processing system, is displayed on a display through a digital-scan converter circuit.

In the probe housing 3, a phase change member 30 is contained together with the transducer unit 28, the flexible printed-wiring board 8 and the magnetic-shield member 12. In order to fix the transducer unit 28, phase change member 30, flexible printed-wiring board 8, cable wires 11, etc. and ensure an insulation in the flexible printed-wiring board 8 signal lines and cable wires 11, the probe housing 3 is filled therein with a filler material 14, such as an urethane resin, having a heat conductivity.

The phase change member 30 is made by a phase change agent 13, changing in phase of from solid to liquid at a particular temperature reached during the operation time period of the transducer 4 and from liquid to solid at lower than the particular temperature, and a film or container 31 accommodating the phase change agent 13. The phase change agent 13 is mixed with a plurality of gas bubbles 32 to permit a volumetric change due to the phase change. Incidentally, the phase change agent 13 may be mixed with a gelling agent. The particular temperature (phase change point), at which the phase change agent 13 is to change in phase, is set at a temperature desirably selected out of the range of 30-50° C. Practically, as the transducer 4 operates, temperature rises in the transducer unit 28, particularly in the acoustic lens 6. When it reaches an upper-limit temperature, say 42° C., or the somewhat lower temperature, say 40° C., the phase change agent 13 reaches a temperature which is set up as a particular temperature (phase change point). The upper-limit temperature, in many cases, is not reached in an operation time period of a pulse-wave mode having a range discrimination for use in an M mode, B mode or color Doppler but reached in an operation time period of a continuous-wave Doppler mode comparatively high in transmission power per unit time.

When the phase change agent 13 reaches the particular temperature, phase change takes place from solid to liquid. On this occasion, considerable great energy is absorbed to exhibit the effect to suppress the surrounding temperature from rising. The effect continues in the duration the phase change agent 13 changes completely into a liquid. The phase change member 30 serves as a thermal buffering agent for buffering the temperature of the transducer 28, particularly of the acoustic lens 6, from rising exceeding the upper-limit temperature (e.g. 42° C.). In other words, the phase change member 30 serves as a thermal delaying agent that acts to delay the transition of the transducer unit 28, particularly the acoustic lens 6, from the state reaching the particular temperature (e.g. 42° C.) into a state exceeding the particular temperature. This can prolong the ultrasonic diagnostic period, say, in the continuous-wave Doppler mode. Otherwise, transmission power can be increased in the pulse-wave/continuous-wave Doppler mode to thereby improve the echo-signal S/N ratio.

Because the phase change point of the phase change agent 13 is set up selectively out of the range of 30-50° C., phase change can be returned from liquid to solid in the temperature environment of lower than the phase change point, i.e. cooling effect can be charged. The phase change agent 13 can be charged a cooling effect even upon examination during non-operation or further the operation at a low transmission power besides in storage.

Next explained is a detailed example of a phase change material used as a phase change agent 13. The phase change material uses, say, "C32" produced by Nippon Blower Co., Ltd. The phase change material C32 has properties explained as follows:
  melting point: 32° C.
  specific gravity: 1.45
  latent heat: 54 Wh/kg
  specific heat: 1 Wh/kg·K.

It is assumed that, in this case, the blower housing 3 has a specific heat of 0.4 [Wh/kg·K] and a specific gravity of 1.08 [g/cm$^3$]. Meanwhile, the backing material 7 is assumed having a specific heat of 0.7 [Wh/kg·K] and a specific gravity of 3 [g/cm$^3$]. The seal-resin material 14 is given a specific heat of 0.53 [Wh/kg·K] and a specific gravity of 0.029 [g/cm$^3$], as noted above.

Provided that the probe proper 2 has a grip (probe housing 3) having a volume of 50 cc, the seal-resin material 14, to fill therein, is in a volume of 20-30 cc. By replacing a portion of 10 cc out of 20-30 cc with phase change material 32C, heat can be absorbed in an amount of approximately 0.78 W owing to latent heat for 1 hour. There are many types of the probe proper 2 wherein heat generation amount differs depending upon the type of the probe proper 2. In case phase change material C32 be used 10 cc for the probe proper 2 that generates a heat of 0.39 W, the temperature interior of the probe proper 2 can be suppressed at 32° C. or lower for 2 hours or longer.

Meanwhile, the product "C48" by Nippon Blower Co., Ltd. is used to suppress the interior temperature of the probe proper 2 at 48° C. or lower. The phase change material C48 has properties as follows:
  melting point: 48° C.
  specific gravity: 1.36
  latent heat: 60 Wh/kg
  specific heat: 1 Wh/kg·K.

Although this embodiment used the phase change material "C32" and "C48" produced by Nippon Blower Co., Ltd., the melt point and latent heat can be changed by changing the phase change material. Accordingly, by using a suitable material, the interior temperature of the blower body 2 can be suppressed at 30° C. or lower or at 30-50° C. for a predetermined time. For example, by using a phase change material having a melting point of 40° C., the interior temperature of the probe proper 2 can be suppressed at 40° C. or lower for a predetermined time. Meanwhile, the embodiment explained the case with a latent heat of 54 [Wh/kg] and 60 [Wh/kg]. However, even with a phase change material having a latent heat lying between those, heat can be absorbed in an amount of the latent heat. The interior temperature of the probe proper 2 can be suppressed from rising.

Incidentally, the phase change material used may have a melting point of 50° C. or higher. Because heat conduction results from the form and interior structure of the probe proper 2, used is a phase change material corresponding to a temperature range of the probe proper 2 in a manner matched to a probe proper 2 design. Accordingly, with a certain interior component arrangement and form of the probe proper 2, the surface temperature of the acoustic lens 6 is possibly suppressed from rising even with using a phase change material having a melting point of 50° C. or higher.

By fixing the interior structure of the probe housing 3 and using, say, a cellular urethane resin as a seal-resin material 14 insulating the flexible printed-wiring board signal line and cable wire 11, the seal resin 14 can be reduced in weight to thereby reduce the weight of the probe proper 2. For example, used is a cellular polystyrene having a latent heat of 0.53 [Wh/kg·K], a specific gravity of 0.029 [g/cm$^3$] and a heat conductivity of 0.038 [W/(mK)]. Because of the specific gravity of 0.029 [g/cm$^3$], the probe proper 2 can be reduced in weight comparatively.

By providing a phase change material in the ultrasonic probe and utilizing the latent heat upon a fusion thereof as described above, the temperature of the ultrasonic probe, particularly the surface temperature of the acoustic lens 6 in contact with an examination subject, can be suppressed from rising. By adjusting the phase change material for its phase change point, cooling effect can be exhibited effectively in a time that temperature is required to suppress from rising. Furthermore, because there is no need to provide a material having a great specific heat (great specific gravity) as used in the existing art, the ultrasonic probe can be reduced in weight.

The phase change agent 13, in this embodiment, is of a phase change material that is in a solid phase at normal temperature but to change in phase from solid to liquid when temperature rises from the normal temperature. The phase change agent 13 returns in phase from liquid to solid at "normal temperature", i.e. at the usual temperature in the environment (in a hospital examination room, or the like) the ultrasonic probe is used. For returning the phase from liquid to solid, there is no need to store the phase change agent 13 in a refrigerator or a freezer. This embodiment utilizes the phenomenon that the phase change agent 13 of a phase change material, raised in temperature from normal temperature, is to absorb heat in an amount of its melting latent heat when melted from solid phase into liquid phase. Even when the interior temperature rises during using the ultrasonic probe, the phase change agent 13 can absorb heat in an amount of melting latent heat due to a phase change of the phase change agent 13 from solid to liquid. Although the rise rate of average temperature relies upon the thermal capacity of the entire ultrasonic probe, the ultrasonic probe can be delayed in its temperature rise rate (particularly, in the surface temperature rise of the acoustic lens in contact with the examination subject). Meanwhile, where temperature rises and falls repeatedly in a certain use state of the ultrasonic probe, it is possible to reduce the surface temperature in the acoustic lens 6. The highest temperature of the acoustic lens 6 can be suppressed to a low level.

Meanwhile, by sealing the phase change agent 13 in a film or container 31 formed of a resin, a metal, graphite or a composite material thereof, the phase change material 13 can be easily provided as a constituent member within the ultrasonic probe. Furthermore, the phase change material 13 after melted can be prevented from moving. Furthermore, by dividing the container 31 into a plurality of segments, the phase change agent 13 can be provided correspondingly to the probe interior even if complex in shape. By using a metal material, such as copper or aluminum, well in heat conductivity as a material for the container 31, heat absorption can be effected efficiently by the phase change material.

Second Embodiment

Figure 2:
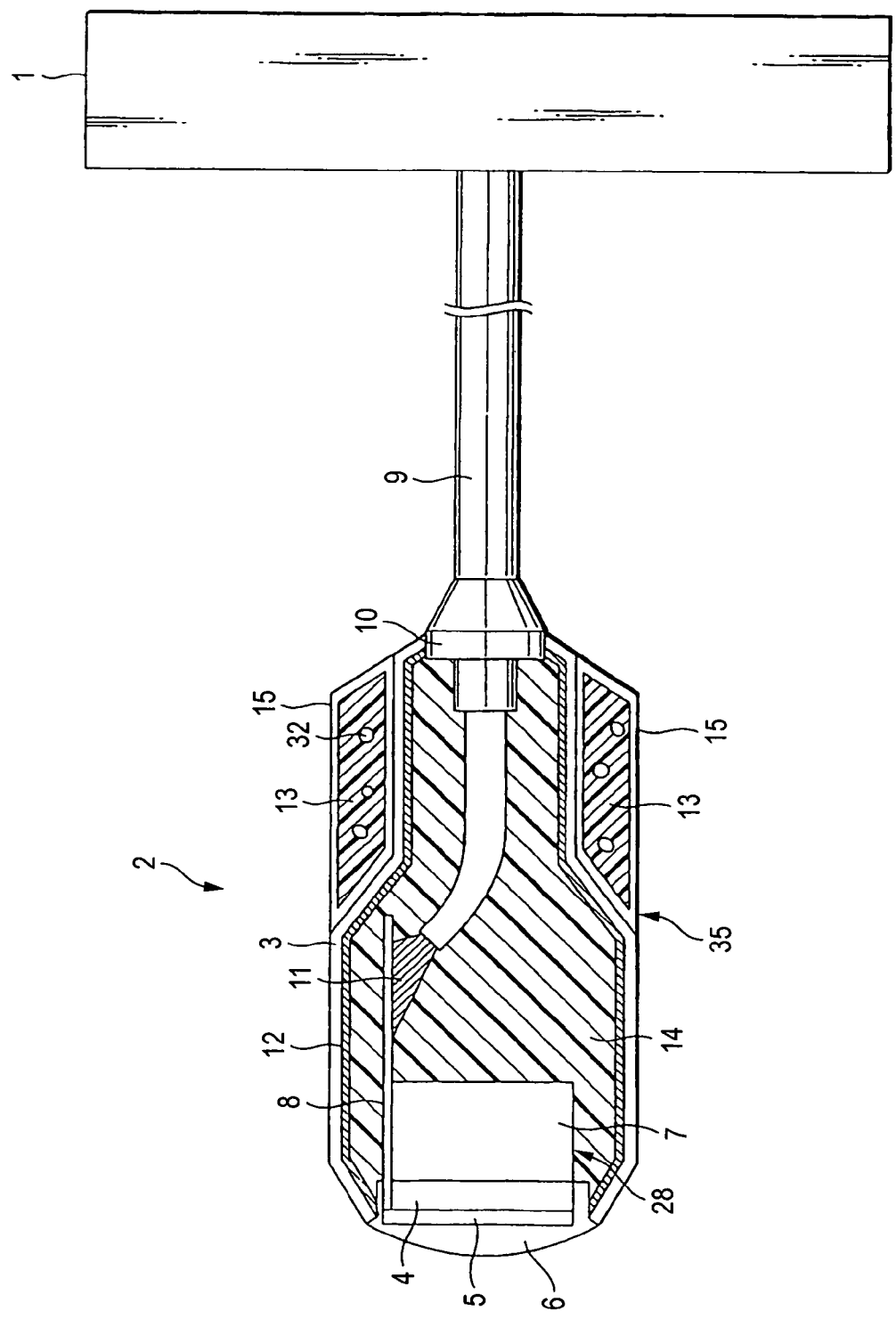
FIG. 2 is a sectional view showing an interior schematic structure of an ultrasonic probe according to a second embodiment in the invention.

An ultrasonic probe in a second embodiment of the invention is explained in its structure while referring to FIG. 2. FIG. 2 is a sectional view showing an interior schematic structure of an ultrasonic probe according to a second embodiment of the invention.

In this embodiment, a phase change member 35 is made up with a phase change agent 13 mixed therein with gas bubbles 32, and a container 15 formed of a resin, a metal, graphite or a composite material thereof and containing the phase change agent 13, as shown in FIG. 2. The phase change member 35 is detachably provided external of the probe housing 3 and close to a cable 9 distant from a transducer unit 28. The phase change material uses a material similar to the first embodiment.

The container 15 is generally in a cylindrical form having an outer shape having a C-form in section partially cut away. The phase change member 35 is arranged to receive the cable 9 at an interior thereof through the cut-out of the container 15. The phase change material 35 can be fit in the rear of the probe proper 2 by a forward movement thereof in a state the cable 9 is received.

By structuring the phase change member 35 removably from the probe proper 2, the phase change member 35 changed into liquid phase can be exchanged with a phase change member 35 in a solid liquid. Meanwhile, it is possible to select and use a phase change member 35 having a suitable phase change point from a plurality of phase change members 35 different in phase change point.

Because the heat generation source of the probe proper 2 lies in its transducer 4, acoustic lens 6 or backing material 7 as described above, the surface temperature is the highest at or around the acoustic lens 6. Meanwhile, in a contact use with an examination subject, the acoustic lens 6 and its periphery contacted with a living body is raised in temperature to a body temperature or its around by the heat of the living body when a certain time is passed even in the absence of heat generation in the transducer 4, etc. Meanwhile, the temperature is lower in a region distant from the acoustic lens 6 because of a heat resistance of the probe proper 2. Consequently, by providing a phase change agent 13 in a position distant from the transducer 4, etc. as in this embodiment, a refrigerant having a low melting point is usable.

Incidentally, "heat resistance" means a coefficient representative of an uneasiness for heat to flow in the application of heat to a certain object, which is expressed in units of K/W or °C./W.

It, if expressed in an equation, is given as heat resistance (°C./W)=temperature difference in the application of heat (°C.)÷heat amount at the heat source (W). The heat resistance is expressed including every situation. Accordingly, heat resistance changes with a structural change of the probe proper 2. For example, in case the materials are changed as to the probe housing 3, the backing material 7, seal-resin material 14, etc. explained in the first embodiment, the heat resistance of the probe proper 2 is changed because of a change in specific heat and heat conductivity.

For example, when the acoustic lens 6 has a surface temperature of 40° C., heat resistance is regulated as to the heat conducting from the transducer 4, etc. to the phase change agent 13 through the probe housing 3 and container 15, thereby regulating the temperature in the region the phase change agent 13 is provided to 32° C. By using a phase change agent 13 having a melting point of 32° C., the surface temperature of the acoustic lens 6 can be maintained at 40° C. under the balance of between a melting of the phase change agent 13 and a heat generation by the transducer 4, etc. In this manner, by placing the phase change agent 13 distant from the transducer 4, etc., the surface temperature of the acoustic lens 6 can be maintained at around 40° C. despite using C32. In this embodiment, the surface temperature of the acoustic lens 6 was 40° C. for the sake of explaining one example. For example, by using a phase change agent 13 having a melting point of 32° C. and regulating the heat resistance, the surface temperature can be given other than 40° C., e.g. 35° C.

Third Embodiment

Figure 3:
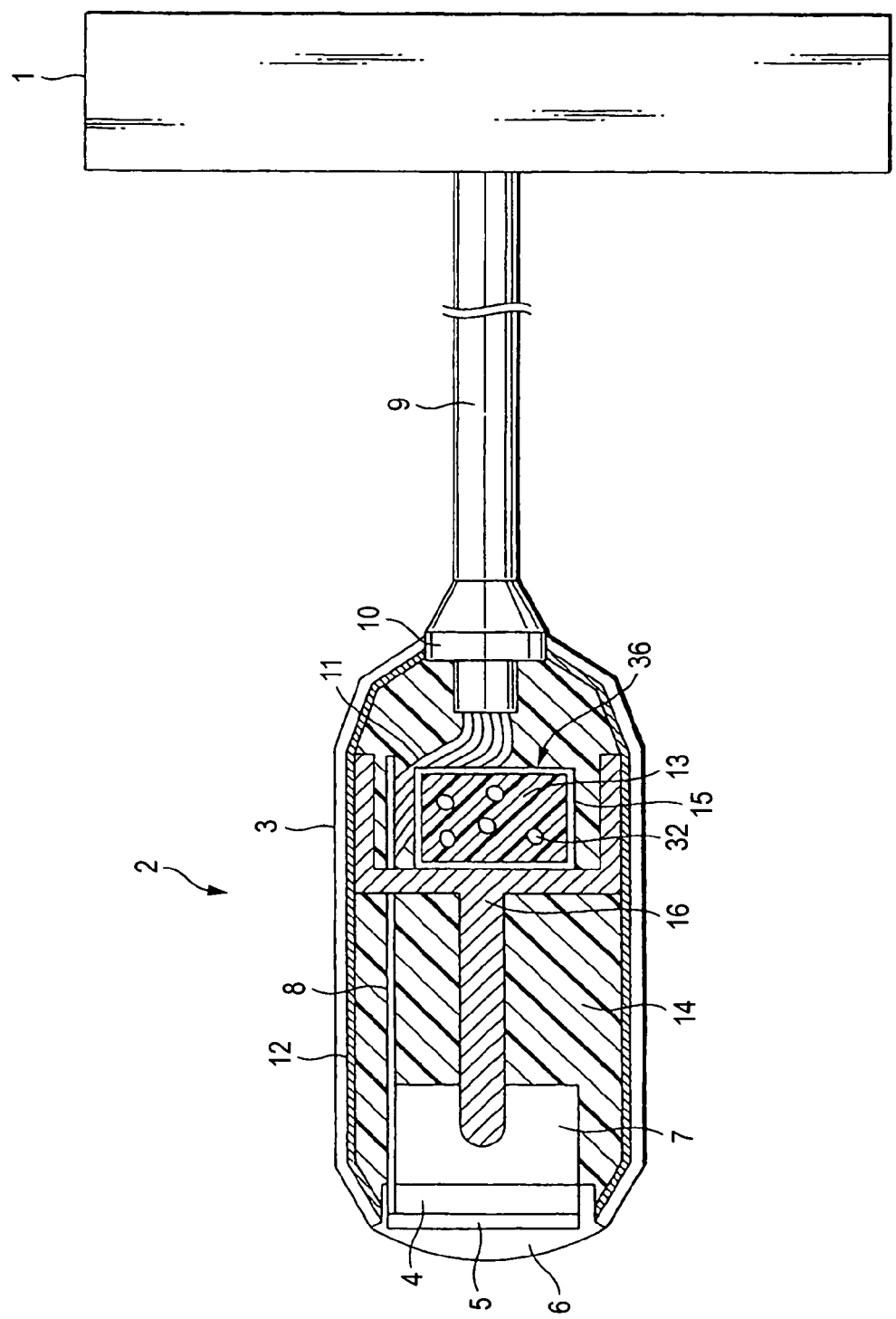
FIG. 3 is a sectional view showing an interior schematic structure of an ultrasonic probe according to a third embodiment in the invention.
Figure 4:
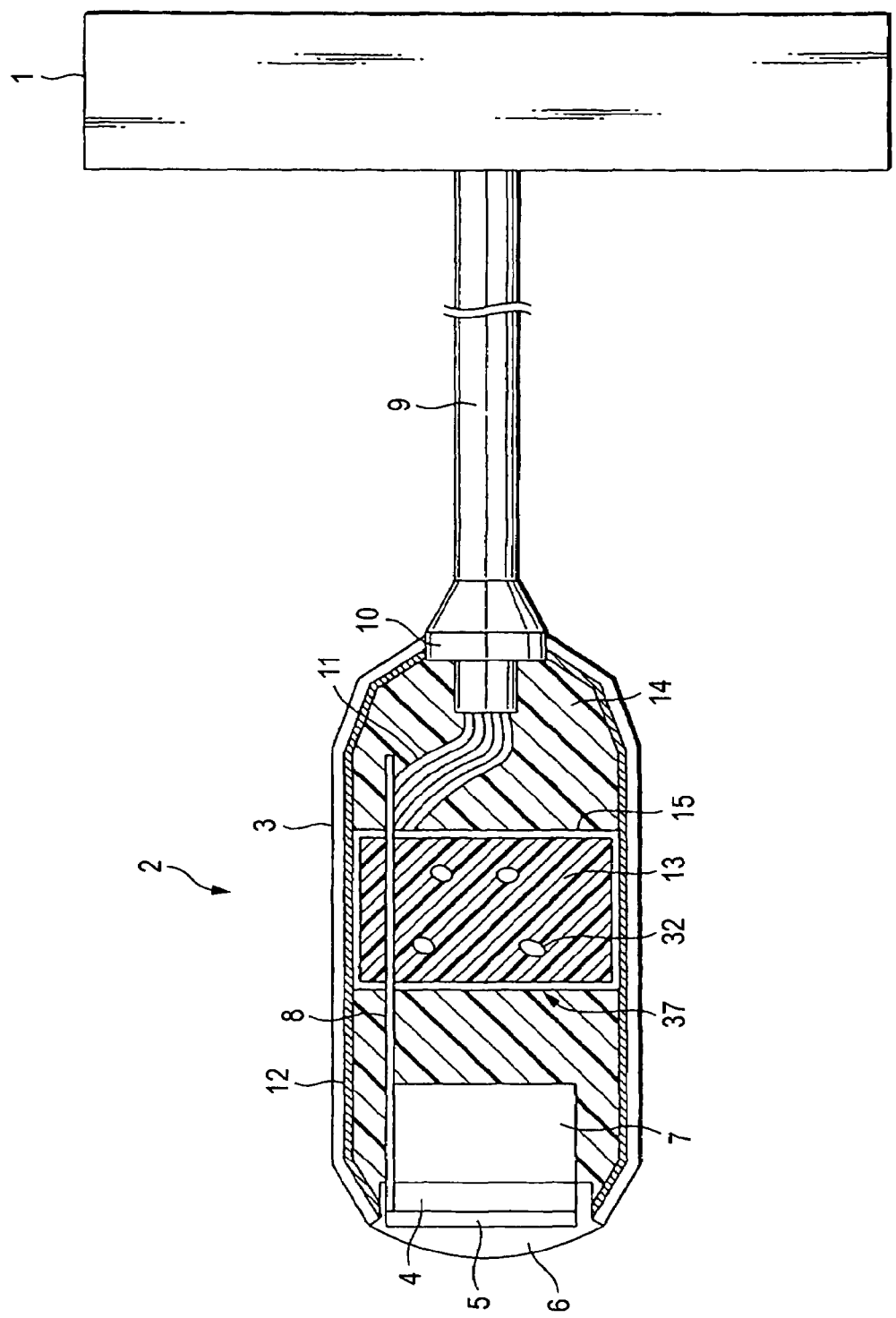
FIG. 4 is a sectional view showing an interior schematic structure of an ultrasonic probe according to the third embodiment in the invention.

An ultrasonic probe in a third embodiment of the invention is explained in its structure while referring to FIGS. 3 and 4. FIGS. 3 and 4 are sectional views showing an interior schematic structure of an ultrasonic probe according to a second embodiment of the invention.

As shown in FIG. 3, a heat pipe (heat conductive member) 16, higher in heat conductivity than a filler agent 14, is provided within a probe proper 2 in this embodiment. The heat conductive member 16 has a generally Y-form. The heat conductive member 16 has one end in contact with or proximity to a backing material 7 bonded to a transducer 4, a heat source. The heat conductive member 16 extends toward the opposite to the transducer 4, i.e. toward a cable 9. The other end of the heat conductive member 16 is branched into a plurality of portions (two in the figure) of the heat conductive member 16 that are in contact with or proximity to side surfaces of a probe housing 3. The heat conductive member 16 is sought of a material low in heat resistance (in other words, a material having a high heat conductivity). For example, it is desired to use graphite or the like besides a metal material, such as aluminum (Al) or copper (Cu), high in heat conductivity. Incidentally, aluminum (Al) is suited for the purpose of suppressing the probe proper 2 from increasing in weight.

The heat conductive member 16 is for allowing to dissipate efficiently the heat of from the transducer 4 acting as a heat source of the probe proper 2 through the surface of the probe housing 3. Namely, the heat conductive member 16 allows to transfer the heat to a point distant from the heat source, thereby increasing the heat-dissipation area.

A container 15, filled with a phase change agent 13 formed of a phase change material, is provided in a manner in contact with or proximity to the heat conductive member 16. The container 15 is structured of aluminum (Al), copper (Cu) or the like. The heat generated at the transducer 4, etc. conducts from one end to the other end of the heat conductive member 16, and further to the container 15 provided in contact with or proximity to the other end thereof. Due to the heat conducted, the phase change agent 13 at a particular temperature changes in phase from solid to liquid, to suppress the temperature increase at the interior of the probe proper 2. Through the heat conductive member 16 having a high heat conductivity, whose one end is in contact with a backing material 7 and the other end is in contact with or proximity to the container 15 receiving the phase change agent 13, the heat generated by the transducer 4 is conducted to the phase change agent 13, thus enhancing the efficiency of heat conduction. This allows the phase change material to efficiently absorb the heat relative to the temperature rise in the probe proper 2. Incidentally, although the phase change member 36 in this embodiment is provided on the other side of the heat conductive member 16, the effect is obtained similarly if it is in contact with or proximity to another point than the other end.

Meanwhile, the effect is obtained similarly even unless separately providing the heat conductive member 16. For example, as shown in FIG. 4, the container 15 accommodating a phase change agent 13, at its one end or both ends, is placed in contact with or proximity to a magnetic-shield member 12. The heat generated by the transducer 4 conducts to the magnetic-shield member 12 through a tip of the magnetic-shield member 12, and further to the container 15 in contact with or proximity to the magnetic-shield member 12. Thus, the heat is conducted to the phase change material 36 received in the container 15. The area of heat dissipation can be increased by the magnetic-shield member 12, thus providing the effect equivalent to the heat conductive member 16. By using a high heat conductive material, such as copper (Cu), for the magnetic-shield member 12, the heat transfer can be enhanced in efficiency of from the transducer 4, etc. as a heat source to the phase change member 36. Thus, the phase change material absorbs heat with efficiency.

Fourth Embodiment

Figure 5:
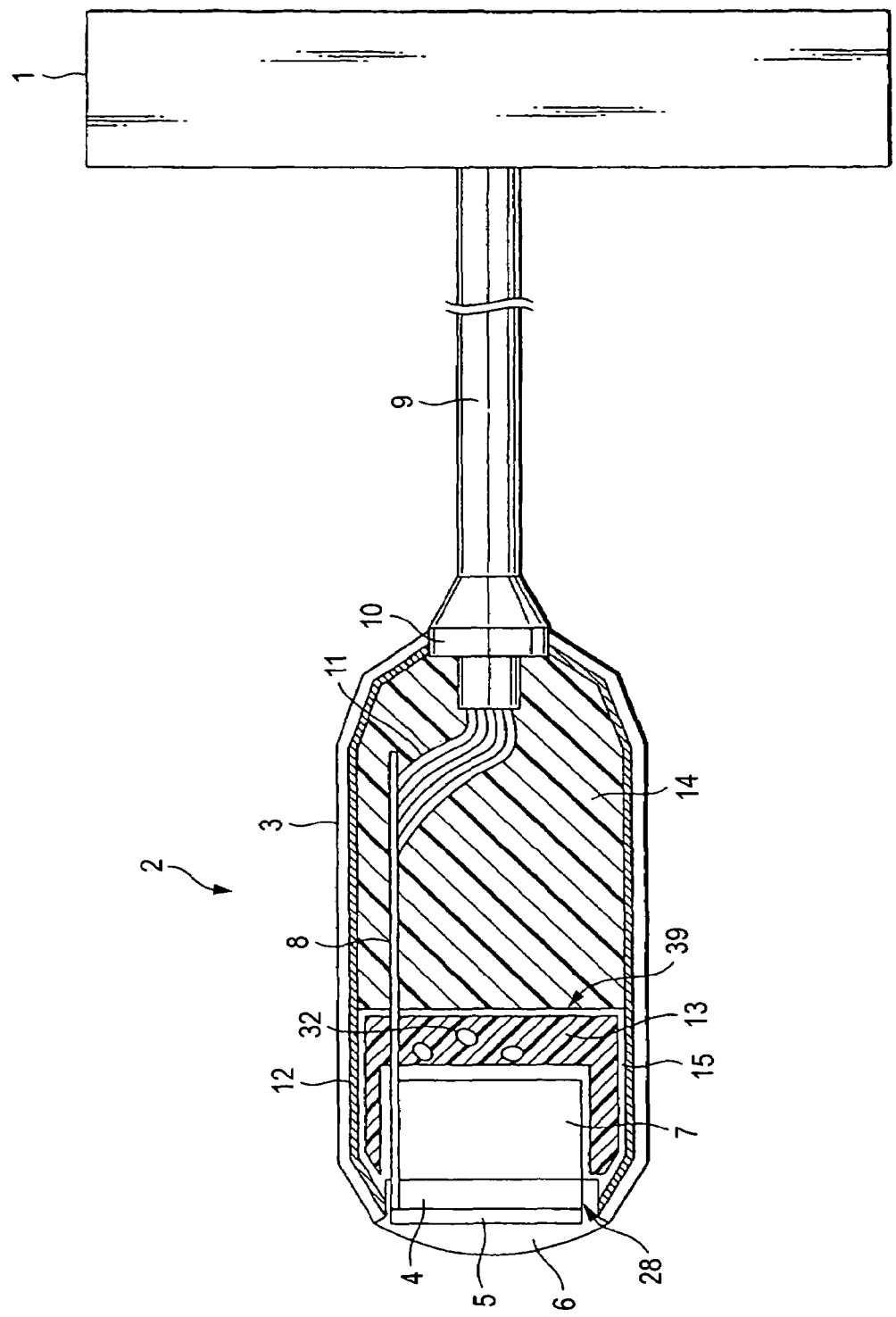
FIG. 5 is a sectional view showing an interior schematic structure of an ultrasonic probe according to a fourth embodiment in the invention.

An ultrasonic probe in a fourth embodiment of the invention is explained in its structure while referring to FIG. 5. FIG. 5 is a sectional view showing an interior schematic structure of an ultrasonic probe according to a fourth embodiment of the invention.

As shown in FIG. 5, a phase change member 39 has a C-form in section. The phase change member 39 is arranged in a manner surrounding the transducer unit 28, particularly a backing member 7 thereof. In order to prevent the melted phase change material from flowing, the phase change material is sealed in a container 15. The container 15 surrounds the transducer 4 and the like. The container 15 is formed of a resin, a metal, graphite or a composite material thereof. In this manner, because the container 15 accommodating a phase change agent 13 is placed in contact with or proximity to the transducer 4, etc., the heat of from the transducer 4, etc. as a heat generation source conducts directly to the phase change agent 13 through the container 15. This can efficiently suppress against the rise in the surface temperature of the acoustic lens 6. Meanwhile, by placing the phase change agent 13 close to the transducer 4, etc., the center of gravity of the probe proper 2 can be neared to the acoustic lens 6, thus improving the operability of the probe proper 2.

Fifth Embodiment

Figure 6:
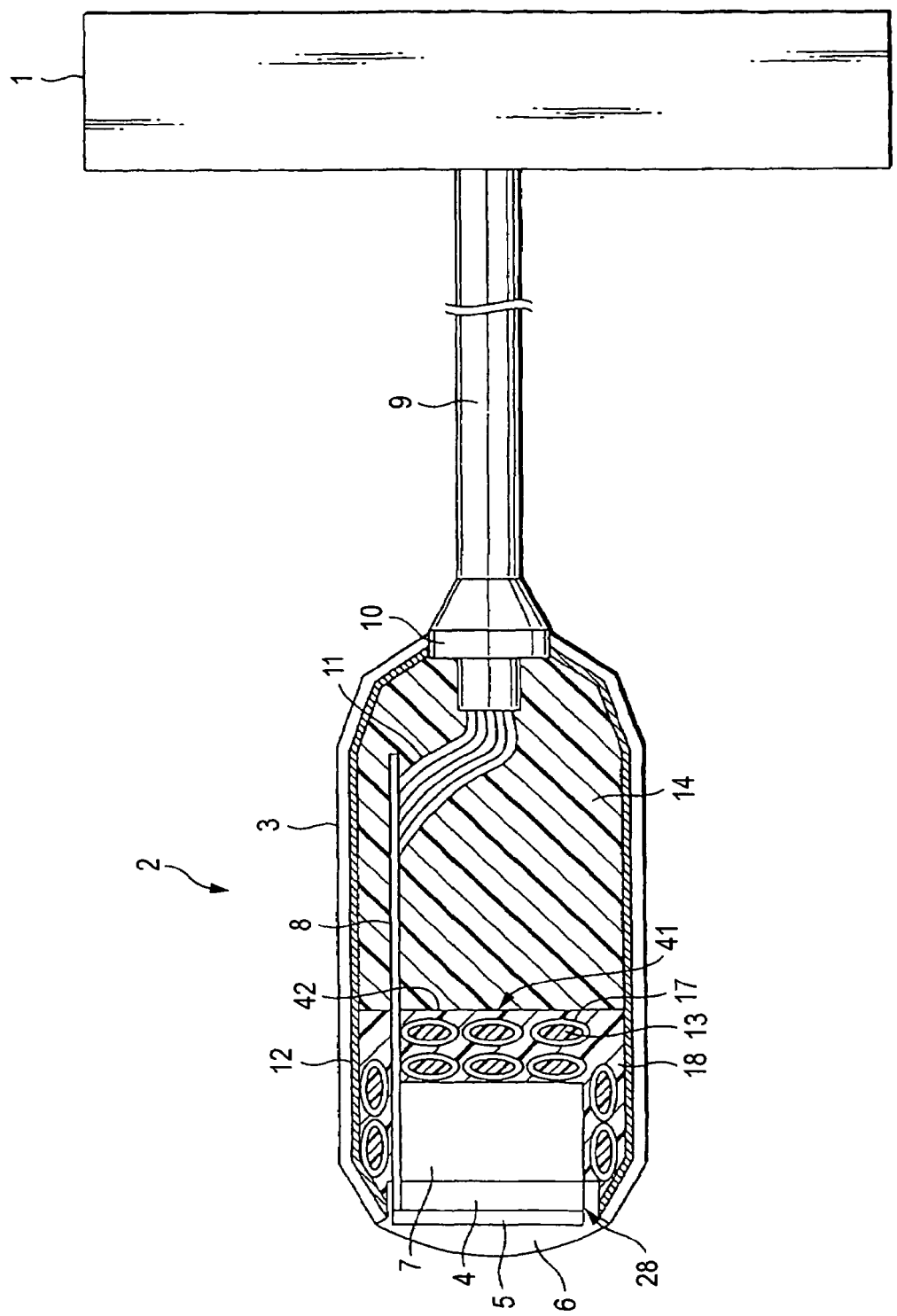
FIG. 6 is a sectional view showing an interior schematic structure of an ultrasonic probe according to a fifth embodiment in the invention.

An ultrasonic probe in a fifth embodiment of the invention is explained in its structure while referring to FIG. 6. FIG. 6 is a sectional view showing an interior schematic structure of an ultrasonic probe according to a fifth embodiment of the invention. As shown in FIG. 6, a phase change member 41 has a C-form in section. The phase change member 41 is arranged in a manner surrounding the transducer unit 28, particularly a backing material 7 thereof. Phase change agent 13 is sealed in capsules 17. A plurality of capsules 17 are accommodated in a container 42. The container 42 is sealed therein with a mold material 18 having a high heat conductivity. The mold material 18 uses an epoxy resin, a silicone resin or the like. For example, by mixing a conductive filler in an epoxy resin, heat conductivity can be given 0.300 [W/(mK)]. Because the seal-resin material 14 has a heat conductivity of 0.038 [W/(mK)] as described above, heat conductivity can be provided higher by the use of the mold material 18 rather than the use of a seal-resin material 14. Incidentally, the mold material 18 has a specific heat of 0.3 [Wh/kg·K] and a specific gravity of 1.850 [g/cm$^3$]. The heat, generated from the transducer 4, etc. as a heat source, conducts to the mold material 18 charged around the capsules 17, and further to the phase change agent 13 internal of the capsules 17 sealed in the mold material 18. By thus arranging the phase change agent 13 around the transducer 4, etc. as a heat generation source, the heat of from the transducer 4, etc. is allowed to directly conduct to the phase change agent 13 through the mold material 18. This can efficiently suppress against the rise in surface temperature of the acoustic lens 6.

Furthermore, by segmenting the phase change agent 13 into a plurality of capsules 17, the phase change member 41 can be easily formed in a form suited for an interior unoccupied chamber of the probe proper 2.

For example, the container 42 used in the probe proper 2 explained in the fourth embodiment has a C-form in section, to have a backing material 7 fit in a recess thereof. However, the container 42 must be made matched to the form of the probe housing 3 or to the form of the transducer 4, the backing material 7 or the like. Namely, because there is a need to make the container 15 in such a form as to surround and contact with the transducer 4, etc., the same container cannot be used if the transducer 4, the probe housing 3 or the like is different in shape. For example, when making a container 42 in a manner matched to the size of a certain transducer 4, backing material 7 or the like and having a recess contacting with and surrounding the transducer 4, backing material 7 or the like, when the container 42 is used for a backing material greater than the backing material 7, its recess cannot be fit over the backing material greater in size. Meanwhile, when the container 42 is used for a backing material smaller in size, a gap occurs at between the recess side surface and the backing material, thus making it difficult to efficiently conduct heat from the transducer 4, etc. to the container 42. In this manner, there is a need to prepare a container 42 for each probe proper 2 different in shape. Thus, there encounters a rise in probe proper 2 manufacturing cost because of a rise in container 42 cost.

Accordingly, by segmenting the phase change agent 13 into capsules 17 and encapsulating around those by a mold material 18, the phase change agent 13 can be easily arranged regardless of the shape of the probe housing 3, the transducer 4, the backing material 7 and the like. This eliminates the need to prepare a container for each different shape of probe proper 2, thus enabling cost reduction.

Figure 7:
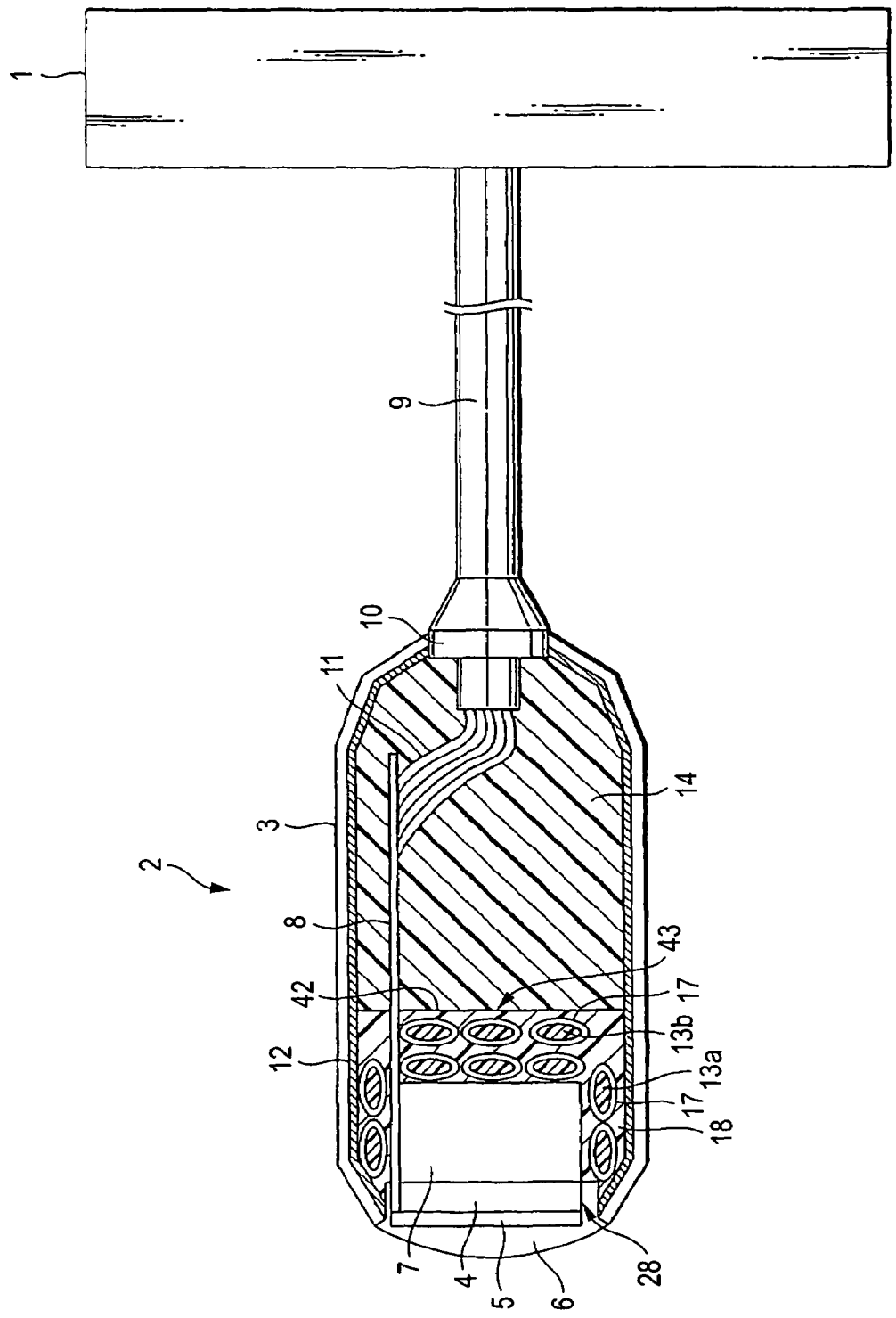
FIG. 7 is a sectional view showing an interior schematic structure of an ultrasonic probe according to the fifth embodiment in the invention.

Furthermore, a plurality of type of phase change materials may be used, as shown in FIG. 7. There are received, in a container 42, capsules 17 sealing therein a first phase change agent 13*a* and capsules 17 sealing therein a second phase change agent 13*b* different in phase change point from the first phase change agent 13*a*.

The phase change agent 13*a* has a phase change point (melting point) set at around 40° C. while the phase change agent 13*b* has a phase change point set at around 48° C. higher than that of the phase change agent 13*a*. The phase change agent 13*a*, having a phase change point of at around 40° C., is provided in order to suppress the surface temperature rise of the acoustic lens 6 in the case the probe proper 2 is driven to be changed in phase with the surface of the examination subject. The phase change agent 13*b*, having a phase change point of at around 48° C., is provided in order to suppress the surface temperature rise of the acoustic lens 6 in a situation that the greater part of an ultrasonic wave generated turned into heat when the probe proper 2 is not in contact with the surface of the examination subject.

In this manner, by using two types or more of phase change agents different in phase change point, even where temperature rise rate or safe surface temperature is different depending upon the situation, e.g. temperature rise in a state contacted with a living body or temperature rise in a state out of contact with a living body, temperature rise can be suppressed in the situation. Meanwhile, temperature rise can be suppressed in accordance with various situations by use of three types or more of phase change materials.

Sixth Embodiment

An ultrasonic probe in a sixth embodiment of the invention is explained in its structure while referring to FIG. 8. FIG. 8 is a sectional view showing an interior schematic structure of an ultrasonic probe according to a sixth embodiment of the invention.

Figure 8B:
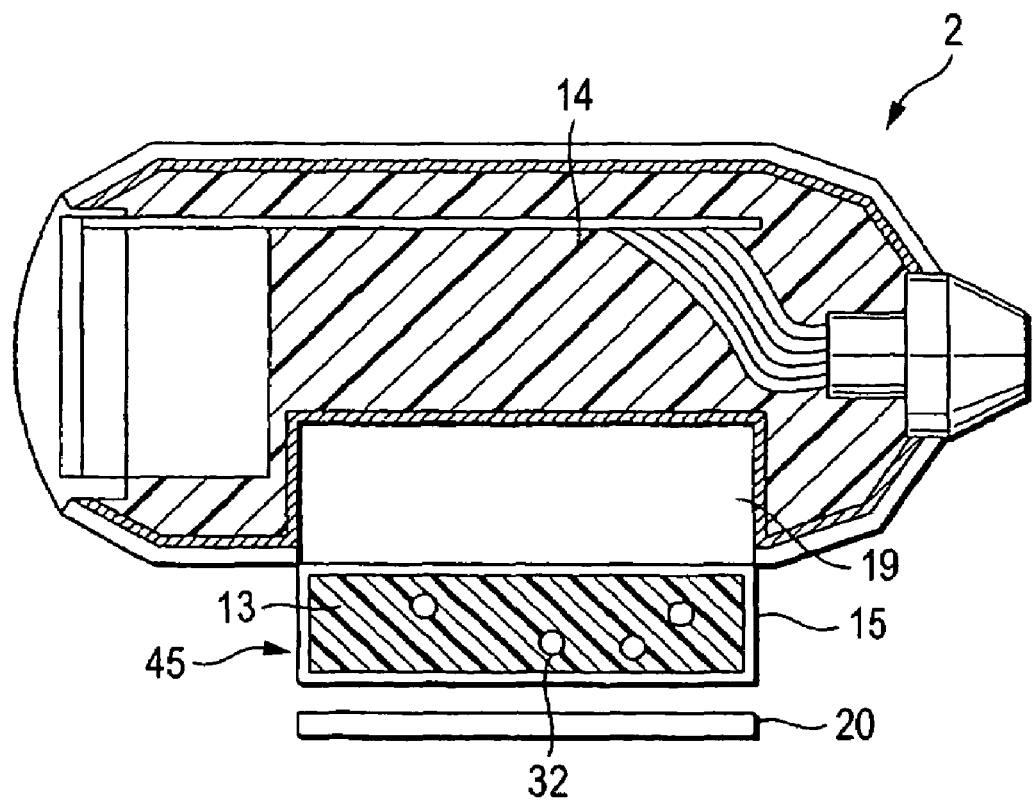
FIG. 8B is a sectional view showing an interior schematic structure of the FIG. 8A ultrasonic probe in a state a phase change member is removed.

In this embodiment, the probe housing 3 at its side surface is formed with a recess 19 to receive a phase change member 45, as shown in FIGS. 8A and 8B. The phase change member 45, having the phase change agent 13 sealed in a container 15, has such a shape as can be received in the recess 19. The recess 19 is closed by a lid 20.

This structure makes it possible to remove the phase change member 45 out of the recess 19 of the probe housing 3, and exchange the phase change member 45. Due to this, even when the probe proper 2 is used for a long time and the phase change agent 13 is weakened in its effect, exchange is possible with another phase change member 45 whose phase change agent 13 is in a solid phase. Without waiting for turning of the phase change agent 13 into a solid phase, the probe proper 2 can be used continuously, thus enabling to continuously suppress against the temperature rise.

Seventh Embodiment

Figure 9:
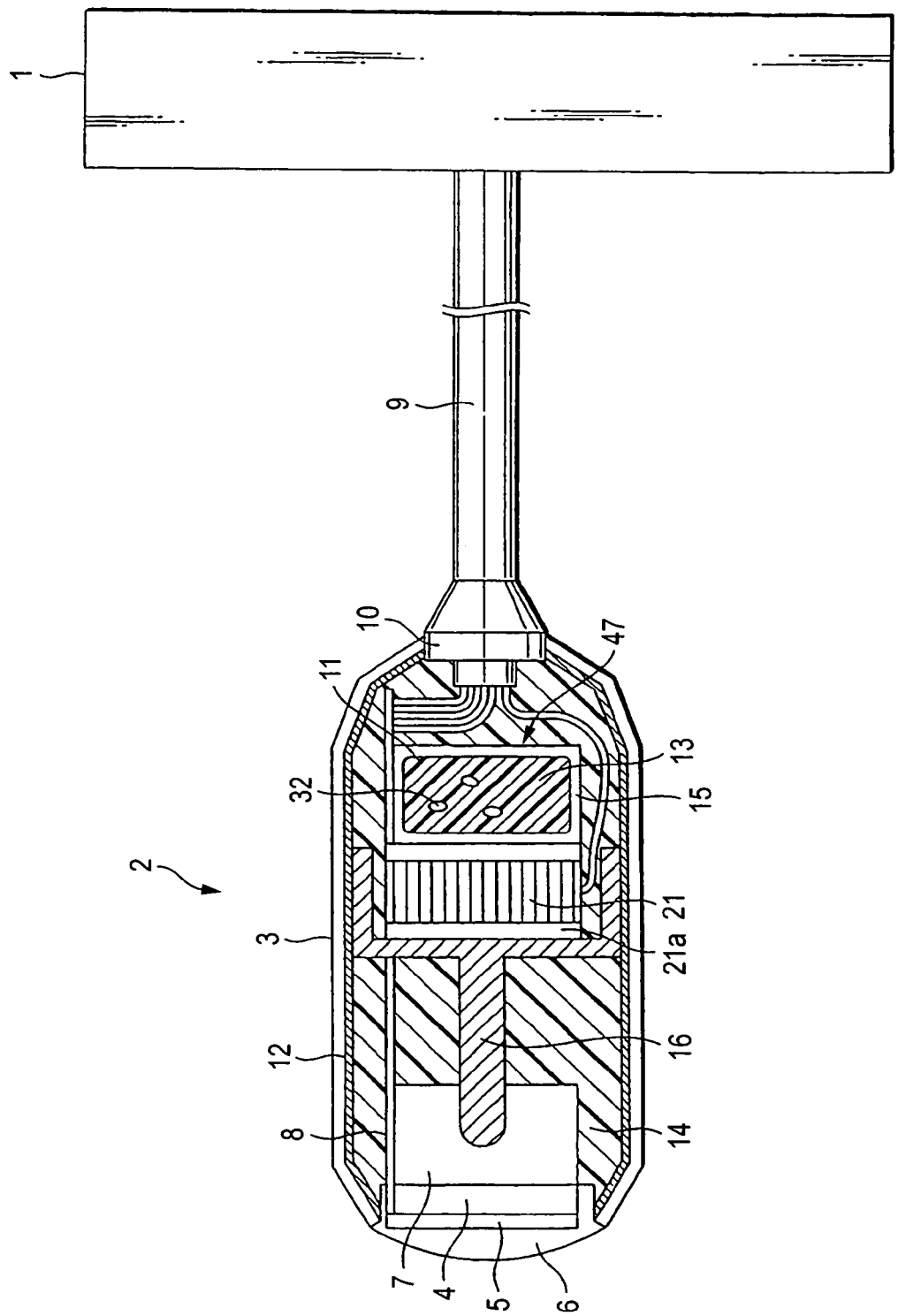
FIG. 9 is a sectional view showing an interior schematic structure of an ultrasonic probe according to a seventh embodiment in the invention.

An ultrasonic probe in a seventh embodiment of the invention is explained in its structure while referring to FIG. 9. FIG. 9 is a sectional view showing an interior schematic structure of an ultrasonic probe according to a seventh embodiment of the invention.

In the interior of the probe housing 3, a cooler 21 is provided not to suppress against the temperature rise but to forcibly decrease the temperature, as shown in FIG. 9. The cooler 21 typically employs a Peltier device. A heat conductive member 16 is provided having one end contacting with a backing material 7 and extending in a direction of the cable 9 and the other end branched into two and contacting with a magnetic-shield member 12. The Peltier device 21 has a heat-absorbing side 21*a* in contact with or proximity to the other end of the heat conductive member 16. Incidentally, the Peltier device 21 corresponds to a "first cooler" in the invention.

When the surface temperature of the probe proper 2 rises, the heat conducts the heat conductive member 16 to reach the other end of the heat conductive member 16. A connector 1 detects a temperature of the probe proper 2 by means of a temperature detector, such as a thermo-couple. By operating the Peltier device 21 from the connector 1, the heat conductive member 16 is cooled to lower the temperature of the probe proper 2. At this time, despite the Peltier device 21 temporarily lowers the temperature of the heat conductive member 16, the temperature is raised by the consumption power of the Peltier device 21 itself. After the passage of a certain degree of time, lost is the capability of cooling the surface temperature of the probe proper 2 (surface temperature of the acoustic lens 6).

For this reason, a phase change agent 13 of a phase change material is provided on the heat dissipation side 21*b* of the Peltier device 21 as in this embodiment, to cool the Peltier device 21. By the cooling, the time the cooling capability is exhibited by the Peltier device 21 can be prolonged. By the effect, the surface temperature of the probe proper 2 (surface temperature of the acoustic lens 6) is lowered. When the Peltier device 21 is ceased from operating, the phase change material dissipates heat slowly and it can restore its cooling capability. For example, in such a case that the surface temperature of the probe proper 2 (surface temperature of the acoustic lens 6) temporarily rises, the cooling mechanism made by the Peltier device 21 can be allowed to operate effectively.

In place of the Peltier device, a coolant-circulation type cooling mechanism may be provided which uses a coolant of water, an alcohol or the like.

Eighth Embodiment

Figure 10A:
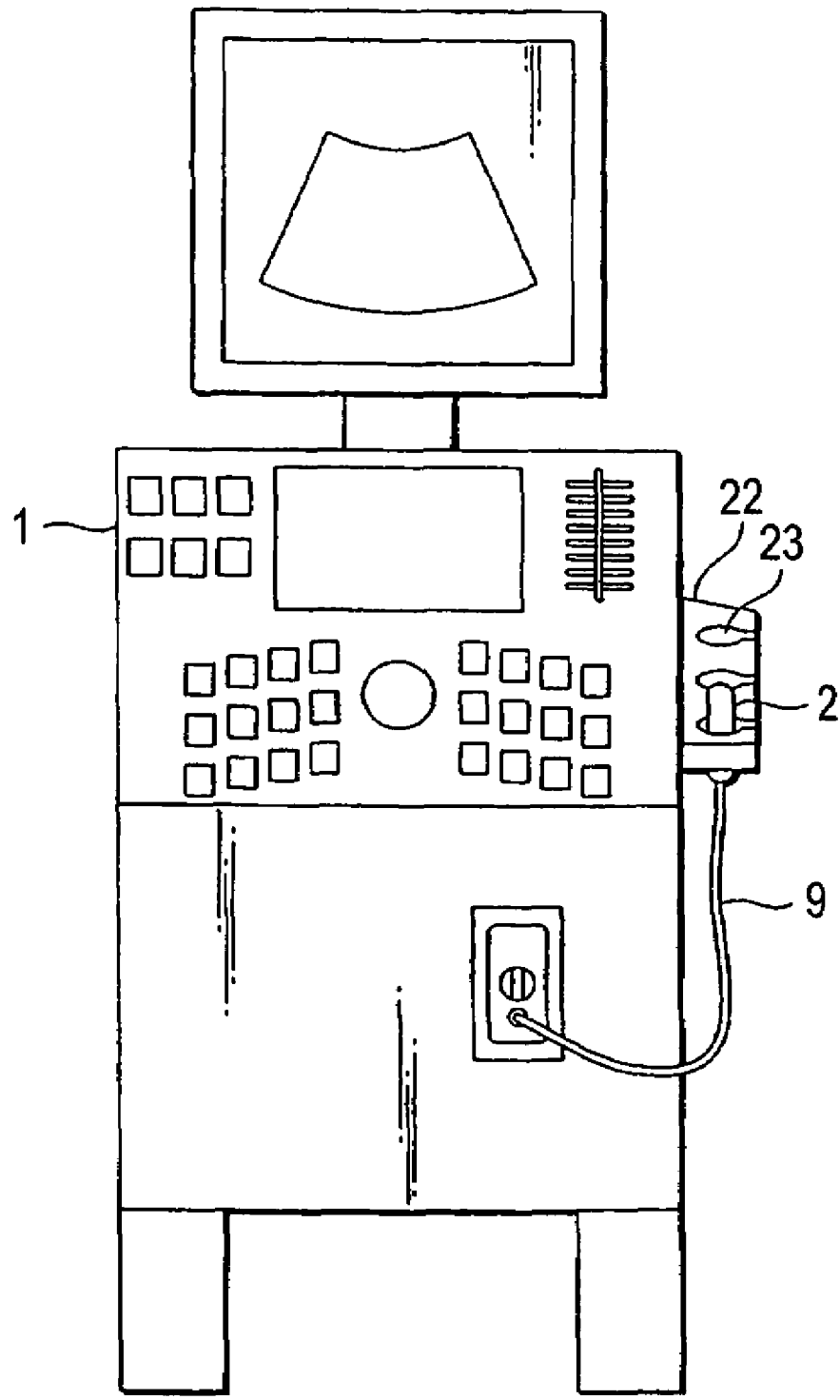
FIG. 10A is a view showing an exterior appearance of an ultrasonic diagnostic apparatus according to an eighth embodiment in the invention.
Figure 10B:
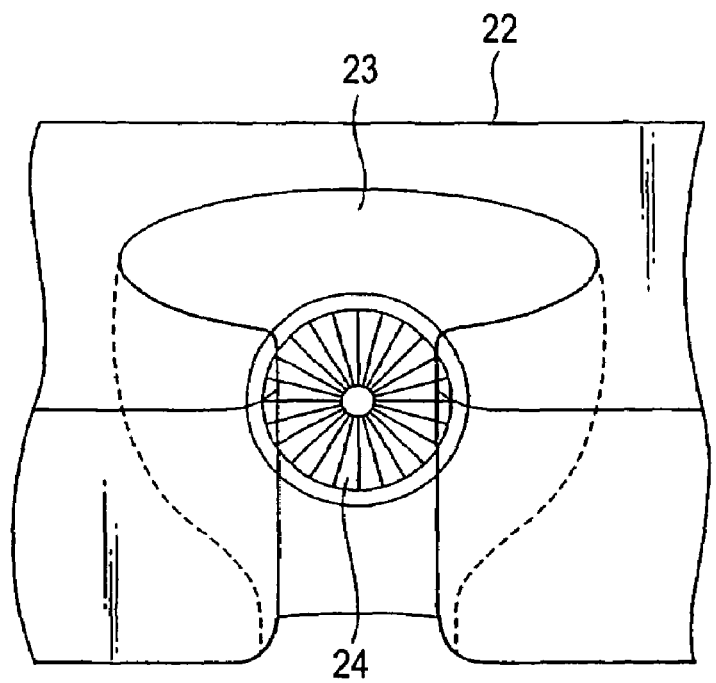
FIG. 10B is a view showing a probe holder in FIG. 10A.
Figure 10C:
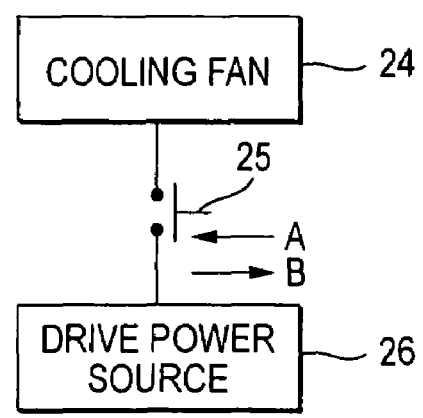
FIG. 10C is a view showing a fan switch in FIG. 10B.
Figure 11:
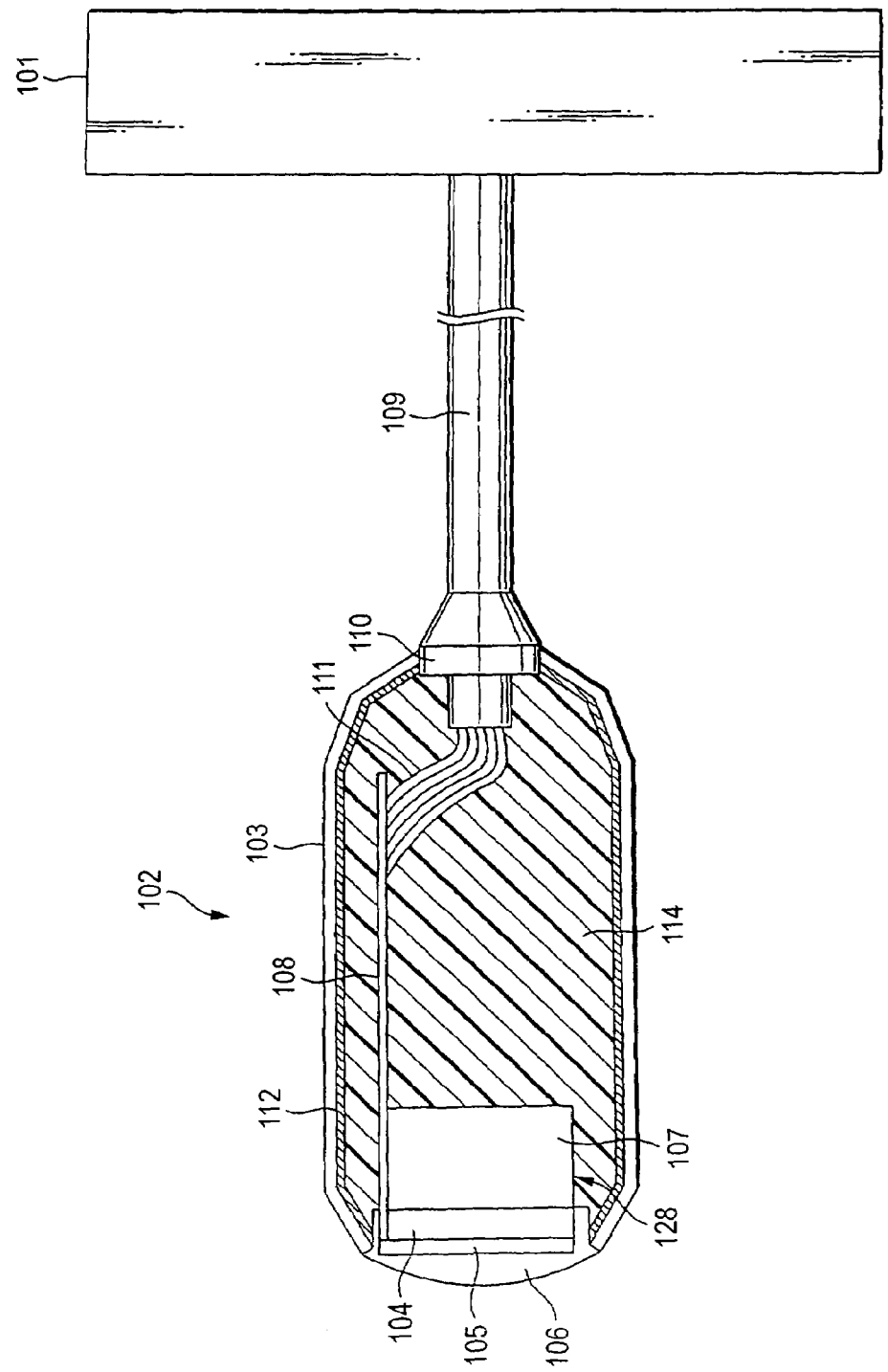
FIG. 11 is a sectional view showing an interior schematic structure of an ultrasonic probe according to a prior art.

An ultrasonic diagnostic apparatus in an eighth embodiment of the invention is explained in its structure while referring to FIGS. 10A, 10B and 10C. As shown in FIG. 10A, a connector 1, at its side surface, is provided with a probe holder 22 where to hold the probe proper 2. The probe holder 22, provided for receiving the probe proper 2, has a hold 23 partly formed with a cutout and penetrating vertically. By inserting the probe proper 2 in the hold 23, the probe proper 2 at its periphery is supported and held by the hold 23. The probe holder 22 corresponds to a "accommodating member" in the invention.

FIG. 10B shows a detailed structure of the hold 23 formed in the probe holder 22. As shown in the figure, the hold 23 penetrates vertically and has a cutout formed in part thereof. Furthermore, a cooling fan 24 is set up in an inner side surface (oppositely to the cutout) of the hold 23. By inserting the probe housing 3 of the probe proper 2 in the hold 23 and supporting the probe housing 3 by the inner side surface, the probe proper 2 is held. The probe housing 3 is inserted in the hold 23 and the probe proper 2 is cooled by the cooling fan 24. Incidentally, the cooling fan 24 corresponds to a "second cooler".

When the probe proper 2 is user for a long time and the temperature of the probe proper 2 entirety is raised, the probe proper 2 even in out of use is in a state temperature is not ready to lower. By providing the cooling fan 24 as a probe cooling mechanism in the probe holder 22 for holding the probe 2 when the probe proper 2 is not used as in this embodiment, the temperature of the probe proper 2 can be lowered. Furthermore, the phase change agent 13 formed of a phase change material provided within the probe housing 3 can be lowered in temperature and returned to the solid phase.

Meanwhile, the cooling fan 24 may be arranged to be automatically driven when the probe proper 2 is inserted in the probe holder 22. For example, a button (not shown) is provided projecting in the inner side surface of the hold 23. When the probe proper 2 is inserted in the hold 23, the button is pushed by the probe housing 3. When the button is pushed, the switch 25 provided in the ultrasonic diagnostic apparatus main body 2 is pushed in the direction of arrow A by the pushing, to connect between the cooling fan 24 and the drive power source 26 supplying power to the cooling fan 24. By the connection, power is supplied from the drive power source 26 to the cooling fan 24, to thereby operating the cooling fan 24. Meanwhile, when the probe proper 2 is removed from the probe holder 22, the switch 25 moves in the direction of arrow B thus returning to the former position. This cuts off the supply of power to the cooling fan 24, thus stopping it from operating.

By thus operating the cooling fan 24 during inserting the probe proper 2 in the probe holder 22 (e.g. when the probe proper 2 is out of use), the temperature of the probe proper 24 can be efficiently lowered. Where the phase change material is melted, it can be restored to the solid phase comparatively in a brief time.

According to the present invention, temperature can be efficiently suppressed from rising exceeding a particular temperature in an ultrasonic prove.

What is claimed is:

1. An ultrasonic probe having a probe proper, a connector and a cable for electrically connecting between the probe proper and the connector, the ultrasonic probe wherein the probe proper comprises:

a transducer that converts between ultrasonic wave and electricity; and a phase change member having a property to cause a phase change of from solid to liquid at a particular temperature reached in an operation time period of the transducer and a phase change of from liquid to solid at lower than the particular temperature, wherein the probe proper further has a probe housing accommodating the transducer, the phase change member having a removavility from the probe housing.

2. An ultrasonic probe having a probe proper, a connector and a cable for electrically connecting between the probe proper and the connector, the ultrasonic probe wherein the probe proper comprises:

a transducer that converts between ultrasonic wave and electricity; and a phase change member having a property to cause a phase change of from solid to liquid at a particular temperature reached in an operation time period of the transducer and a phase change of from liquid to solid at lower than the particular temperature, wherein the probe proper further has a probe housing accommodating the transducer, the phase change member being received in a recess formed in a side surface of the probe housing.

3. An ultrasonic probe having a probe proper, a connector and a cable for electrically connecting between the probe proper and the connector, the ultrasonic probe wherein the probe proper comprises:

a transducer that converts between ultrasonic wave and electricity; and a phase change member having a property to cause a phase change of from solid to liquid at a particular temperature reached in an operation time period of the transducer and a phase change of from liquid to solid at lower than the particular temperature, wherein the phase change member is connected to the transducer through a heat pipe.

4. An ultrasonic probe having a probe proper, a connector and a cable for electrically connecting between the probe proper and the connector, the ultrasonic probe wherein the probe proper comprises:

a transducer that converts between ultrasonic wave and electricity; and a phase change member having a property to cause a phase change of from solid to liquid at a particular temperature reached in an operation time period of the transducer and a phase change of from liquid to solid at lower than the particular temperature, wherein the probe proper further has a probe housing accommodating the transducer and a magnetic-shield member formed on an inner surface of the probe housing, the phase change member being connected to the transducer through the magnetic-shield member.

5. An ultrasonic probe having a probe proper, a connector and a cable for electrically connecting between the probe proper and the connector, the ultrasonic probe wherein the probe proper comprises:

a transducer that converts between ultrasonic wave and electricity; and a phase change member having a property to cause a phase change of from solid to liquid at a particular temperature reached in an operation time period of the transducer and a phase change of from liquid to solid at lower than the particular temperature, wherein the probe proper further has a probe housing accommodating the transducer and a cooler arranged in the probe housing, the phase change member being placed in contact with a heat dissipation surface of the cooler.

6. An ultrasonic probe according to claim 5, wherein the cooler has a Peltier device.

7. An ultrasonic probe according to claim 5, wherein the cooler is a heat exchanger of a cooling mechanism of a coolant-circulation type.

* * * * *